US011928899B2

(12) United States Patent
Singh et al.

(10) Patent No.: US 11,928,899 B2
(45) Date of Patent: Mar. 12, 2024

(54) METHOD AND SYSTEM FOR PROVISIONING CLOUD SERVICE ON VEHICLE

(71) Applicant: Accenture Global Solutions Limited, Dublin (IE)

(72) Inventors: Paul Sundar Singh, Chennai (IN); Manisha Suri Sriraman, Bangalore (IN); Abhilash Manu, Bangalore (IN); Deepa Rajendran, Chennai (IN); Divyanshu Shekhar, Bangalore (IN); Avanish Singh, Bengaluru (IN)

(73) Assignee: ACCENTURE GLOBAL SOLUTIONS LIMITED, Dublin (IE)

( * ) Notice: Subject to any disclaimer, the term of this patent is extended or adjusted under 35 U.S.C. 154(b) by 238 days.

(21) Appl. No.: 17/401,157

(22) Filed: Aug. 12, 2021

(65) Prior Publication Data
US 2022/0177003 A1 Jun. 9, 2022

(30) Foreign Application Priority Data
Dec. 7, 2020 (IN) .............................. 202041053127

(51) Int. Cl.
*G07C 5/00* (2006.01)
*B60W 40/04* (2006.01)
(Continued)

(52) U.S. Cl.
CPC ............ *G07C 5/008* (2013.01); *B60W 40/04* (2013.01); *B60W 40/08* (2013.01); *B60W 50/02* (2013.01);
(Continued)

(58) Field of Classification Search
CPC ....... G07C 5/008; B60W 40/08; B60W 40/04; B60W 50/02; B60W 60/001;
(Continued)

(56) References Cited

U.S. PATENT DOCUMENTS 5,852,630 A * 12/1998 Langberg ............ H04L 27/2647
375/219
8,311,526 B2 11/2012 Forstall et al.
(Continued)

OTHER PUBLICATIONS

Kushani Perera et al., "An Intelligent Driver Guidance Tool using Location Based Services", Dialog Mobile Communications Research Laboratory, University of Moratuwa University of Moratuwa, Moratuwa, Sri Lanka; Electronic and Telecommunication Department, University of Moratuwa University of Moratuwa, Moratuwa, Sri Lanka; Downloaded on Nov. 11, 2020 at 23:14:43 UTC from IEEE Xplore, pp. 246-251 (6 pages total).
"Car UI Library Integration Guide", Android Open Source Project, (https://source.android .com/devices/automotive/hmi/car _ ui), 3 pages, Downloaded Nov. 11, 2020.
(Continued)

*Primary Examiner* — Hirdepal Singh
(74) *Attorney, Agent, or Firm* — Crowell & Moring LLP (57) ABSTRACT

Embodiments of this disclosure disclose provisioning a cloud service on a vehicle. The method may include, in response to receiving a registration request for cloud services for a vehicle and determining a geographical location of the vehicle based on the registration request. The method may further include identifying cloud services available to the geographical location and extracting capability information of the vehicle from real time series data of the vehicle. The method may further include determining cloud services applicable to the vehicle from the cloud services available to the geographical location based on the extracted capability information of the vehicle and in response to receiving a service subscription request from the vehicle, provisioning on the vehicle a cloud service applicable to the vehicle corresponding to the service subscription request.

20 Claims, 7 Drawing Sheets

(51) Int. Cl.

| | |
|---|---|
| *B60W 40/08* | (2012.01) |
| *B60W 50/02* | (2012.01) |
| *B60W 60/00* | (2020.01) |
| *G01C 21/34* | (2006.01) |
| *G01C 21/36* | (2006.01) |
| *G06F 16/22* | (2019.01) |
| *G06F 16/29* | (2019.01) |
| *G06Q 40/08* | (2012.01) |
| *G16H 40/20* | (2018.01) |
| *G16H 40/67* | (2018.01) |

(52) U.S. Cl.
CPC ....... *B60W 60/001* (2020.02); *G01C 21/3415* (2013.01); *G01C 21/3691* (2013.01); *G06F 16/22* (2019.01); *G06F 16/29* (2019.01); *G06Q 40/08* (2013.01); *G16H 40/20* (2018.01); *G16H 40/67* (2018.01); *B60W 2556/45* (2020.02)

(58) Field of Classification Search
CPC ........... B60W 2556/45; G01C 21/3415; G01C 21/3691; G06F 16/22; G06F 16/29; G06Q 40/08; G16H 40/20; G16H 40/67; G16H 40/63; G16H 50/20
USPC .................................................... 455/456.1
See application file for complete search history.

(56) References Cited

U.S. PATENT DOCUMENTS

| | | | |
|---|---|---|---|
| 9,298,985 B2 | 3/2016 | Krueger | |
| 10,915,101 B2* | 2/2021 | Cohen | G06V 20/58 |
| 2009/0079555 A1 | 3/2009 | Aguirre De Carcer et al. | |
| 2013/0304863 A1* | 11/2013 | Reber | H04L 67/10 |
| | | | 709/218 |
| 2021/0110503 A1* | 4/2021 | Koda | G06Q 50/30 |
| 2021/0392496 A1* | 12/2021 | Vladimerou | H04W 12/61 |

OTHER PUBLICATIONS

Pooja Singal et al., "Dijkstra Shortest Path Algorithm using Global Positioning System", International Journal of Computer Applications (0975-8887), vol. 101—No. 6, Sep. 2014, pp. 13-18.

S. F. Liang et al., "Monitoring Driver's Alertness Based on the Driving Performance Estimation and the EEG Power Spectrum Analysis", Proceedings of the 2005 IEEE, Engineering in Medicine and Biology 27th Annual Conference Shanghai, China, Sep. 1-4, 2005, Downloaded on Nov. 11, 2020 at 23:11:38 UTC from IEEE Xplore, pp. 5738-5741 (4 pages).

"Smart City Mobility", Smart City Car: Connected, Intelligent, Integrated, HEREMobility, https://mobility.here.com/learn/smart-city-mobility/smart-city-car-connected, Downloaded Nov. 9, 2020, 10 pages total.

"Remote Driving System", Soliton, https://solitonsys.com/wp-content/themes/soliton-systems/pdf/Remote_Driving_Brochure.pdf, Downloaded Nov. 9, 2020, 4 pages total.

\* cited by examiner

METHOD AND SYSTEM FOR PROVISIONING CLOUD SERVICE ON VEHICLE

RELATED APPLICATION

This application claims priority to Indian Provisional Patent Application No. 202041053127, entitled "SMART INTEGRATED VEHICLE SERVICE" filed on Dec. 7, 2020, wherein the entirety of the above-referenced application is incorporated herein by reference.

TECHNICAL FIELD

This application generally relates to the intelligent vehicle. In particular, this application describes a method and system for provisioning a cloud service on a vehicle.

BACKGROUND

As automotive giants rally to indulge customers with varied features in their vehicles, the biggest change that is occurring currently in the automobiles is autonomy. Given the current premise, the software pushed down to the electronic control module of a vehicle is limited to the architecture that is tightly coupled with the offerings for the brand of the vehicle. This restricts the customers from realizing the benefits of technological advancement available across the automotive industries.

SUMMARY

This disclosure relates to systems and methods for provisioning a cloud service on a vehicle.

In one embodiment, a method for provisioning a cloud service on a vehicle is disclosed. The method may include, in response to receiving a registration request for cloud services for a vehicle, determining, with a processor circuitry of a cloud server communicatively coupled with the vehicle, a geographical location of the vehicle based on the registration request. The method may further include identifying, with the processor circuitry, cloud services available to the geographical location and extracting, with the processor circuitry, capability information of the vehicle from real time series data of the vehicle. The real time series data may include data generated by functional units of the vehicle in operation of the vehicle. The method may further include determining, with the processor circuitry, cloud services applicable to the vehicle from the cloud services available to the geographical location based on the extracted capability information of the vehicle and in response to receiving a service subscription request from the vehicle, provisioning, with the processor circuitry, on the vehicle a cloud service applicable to the vehicle corresponding to the service subscription request.

In another embodiment, a system for provisioning a cloud service on a vehicle is disclosed. The system may include a memory having stored thereon executable instructions and a processor in communication with the memory. When executing the instructions, the processor may be configured to, in response to receiving a registration request for cloud services for a vehicle, determine a geographical location of the vehicle based on the registration request. The processor may further be configured to identify cloud services available to the geographical location and extract capability information of the vehicle from real time series data of the vehicle. The real time series data may include data generated by functional units of the vehicle in operation of the vehicle. The processor may further be configured to determine cloud services applicable to the vehicle from the cloud services available to the geographical location based on the extracted capability information of the vehicle and in response to receiving a service subscription request from the vehicle, provision on the vehicle a cloud service applicable to the vehicle corresponding to the service subscription request.

In another embodiment, a product for provisioning a cloud service on a vehicle is disclosed. The product may include machine-readable media other than a transitory signal and instructions stored on the machine-readable media. When being executed, the instructions may be configured to cause a processor to, in response to receiving a registration request for cloud services for a vehicle, determine a geographical location of the vehicle based on the registration request. The processor may further be configured to identify cloud services available to the geographical location and extract capability information of the vehicle from real time series data of the vehicle. The real time series data may include data generated by functional units of the vehicle in operation of the vehicle. The instructions may further be configured to cause the processor to determine cloud services applicable to the vehicle from the cloud services available to the geographical location based on the extracted capability information of the vehicle and in response to receiving a service subscription request from the vehicle, provision on the vehicle a cloud service applicable to the vehicle corresponding to the service subscription request.

One interesting feature of the systems and methods described below may be that it may provision vehicle OEM agnostic or brand neutral cloud services on different brands of vehicles. In particular, the systems and methods may offer a configurable set of cloud services in terms of applicability of intelligent cloud service functionalities to the feasible vehicle models. This offers the vehicle OEM the possibility to connect with internet of things (IoT) platforms without changing its underlying vehicle design to adapt to the IoT platforms. Additionally, in the absence of stable network connection between the vehicle and the IoT platforms, the data from the vehicles may be stored locally on the IoT platforms which is thus able to apply artificial intelligence on the dataset to provide the desired cloud service outcome. Also, the systems and methods may improve the driving experience of the vehicle by provisioning advanced safety cloud services based on the real time series data from the vehicle such as health monitoring service and teleoperation service. Moreover, the vehicle may be provided with cloud services of the IoT platforms by submitting cloud service subscription and thus is able to readily switch on/off the consumption of the cloud services.

The above embodiments and other aspects and alternatives of their implementations are explained in greater detail in the drawings, the descriptions, and the claims.

BRIEF DESCRIPTION OF THE DRAWINGS

The present disclosure may be better understood with reference to the following drawings and description. The components in the figures are not necessarily to scale. Moreover, in the figures, like-referenced numerals designate corresponding parts throughout the different views.

DETAILED DESCRIPTION

At present, vehicle OEMs play the differentiating role of offering different smart and autonomous features in their brand of vehicles. At the back, different services that are being offered are result of collaboration between a third-party vendor and an OEM. Even though connected features vary by brand, but they offer similar experience to end customers. One of the objectives of the present disclosure is to provision OEM agnostic or brand neutral cloud services on different brands of vehicles.

Figure 1:
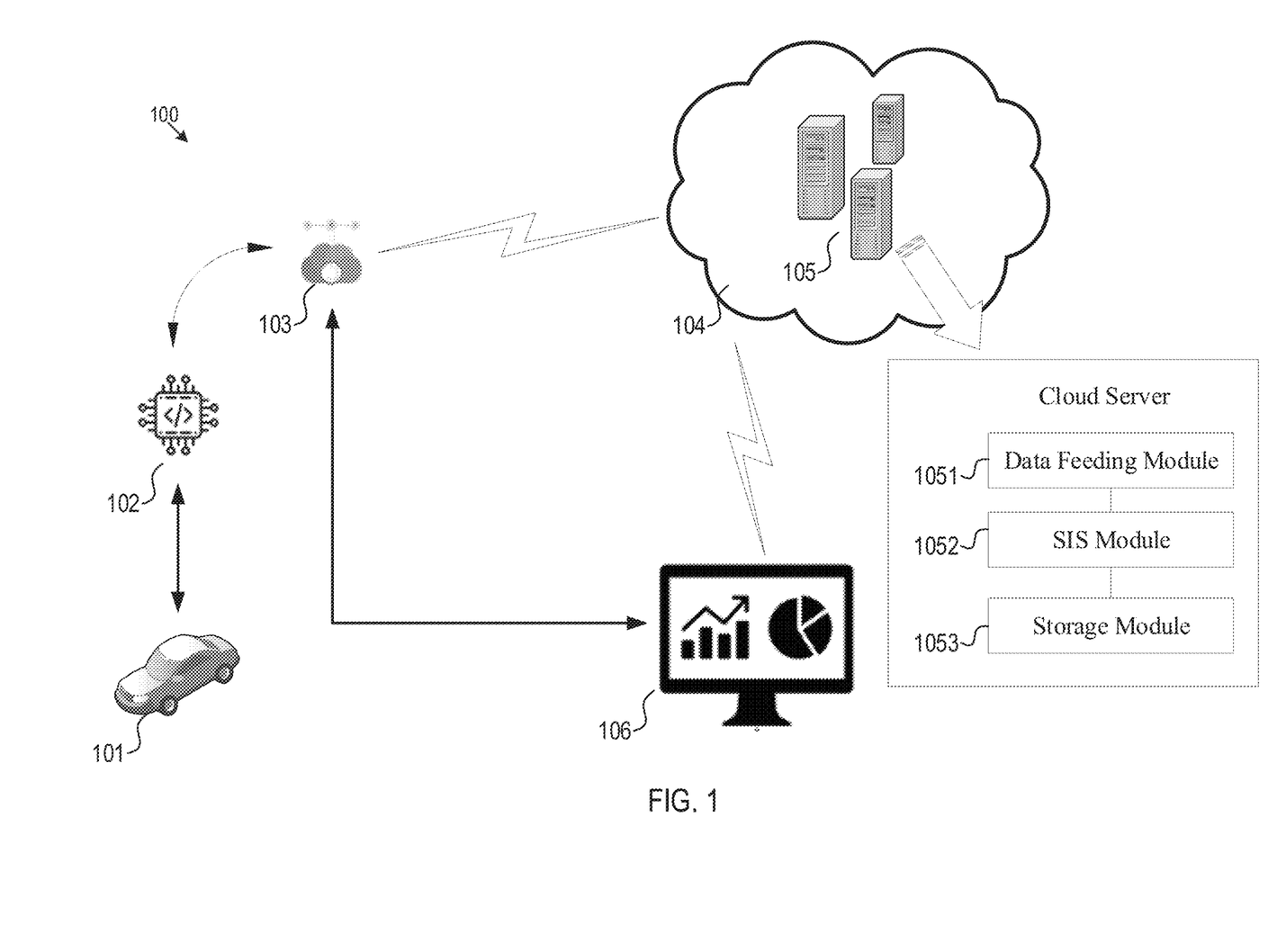
FIG. 1 illustrates an exemplary application architecture for the vehicle cloud service provisioning system in accordance with an embodiment.

FIG. 1 illustrates an exemplary application architecture of an internet of things (IoT) system 100 for provisioning a cloud service on a vehicle. The system 100 may include a vehicle 101, an electronic control module (ECM) 102, an IoT cloud 104, and a cloud server 105. The electronic control module 102 may be integrated into the vehicle 101, which may represent an embedded system in automotive electronics that controls one or more of the electrical systems or subsystems in the vehicle 101. The electronic control module 102 may include engine control module, powertrain control module, transmission control module, brake control module, central control module, central timing module, general electronic module, body control module, and suspension control module. The IoT cloud 104 may represent a massive network that supports IoT devices and applications. It may include the underlying infrastructure, servers and storage, needed for real-time operations and processing. The IoT cloud 104 may also include the cloud services and standards necessary for connecting, managing, and securing different IoT devices and applications.

The cloud server 105 may be deployed on the IoT cloud 104 and may include the data feeding module 1051, the smart integrated service (SIS) module 1052, and the storage module 1053. The functions of the individual modules will be discussed with reference an example cloud service provisioning (CSP) logic 200 executed by the cloud server 105 in FIG. 2. It should be appreciated that the individual modules may be implemented in the same cloud server or different cloud servers on the IoT cloud. The logical features of the CSP logic 200 may be implemented in various orders and combinations.

Figure 2:
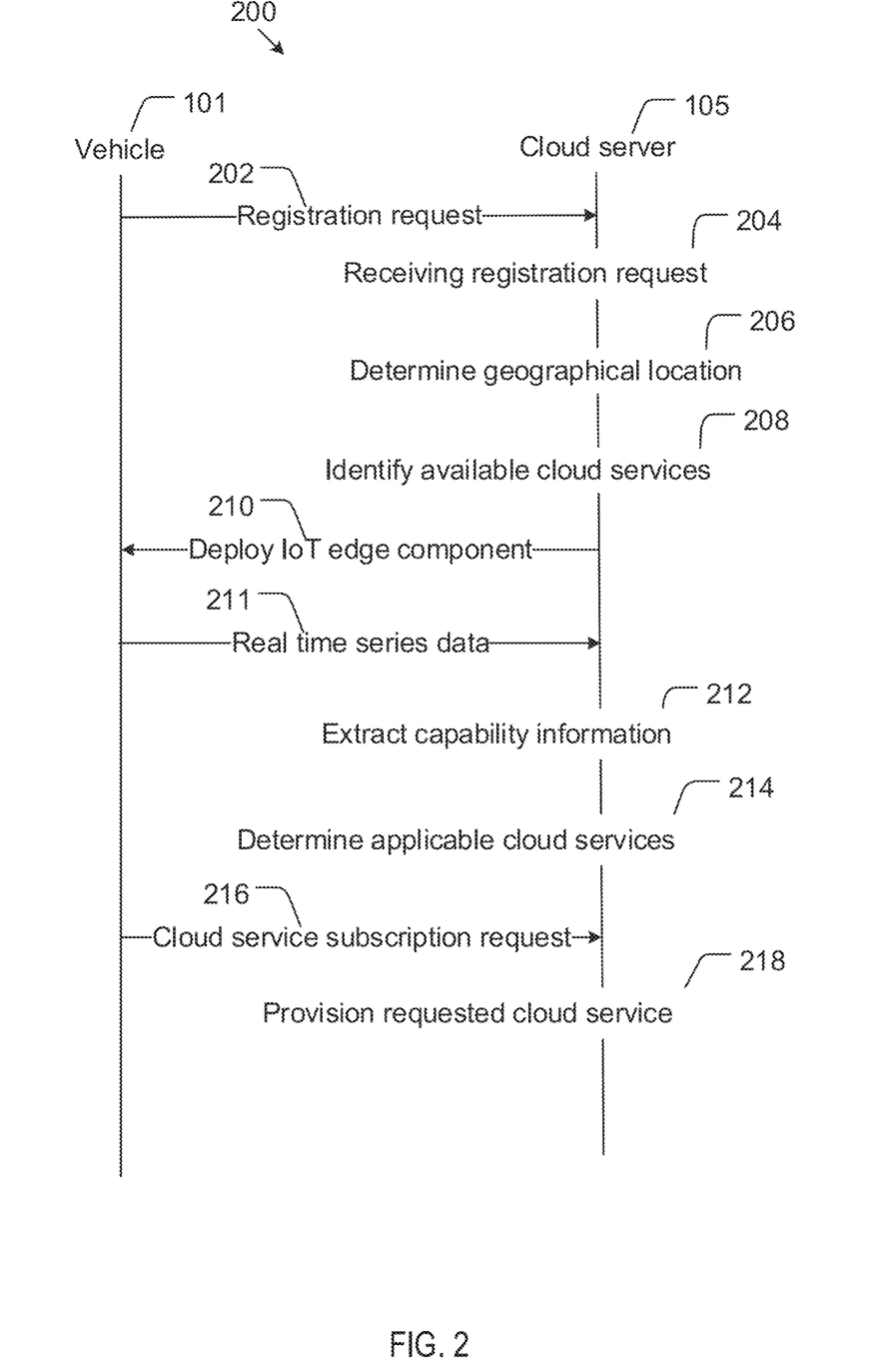
FIG. 2 illustrates a data flow diagram for provisioning a cloud service on a vehicle in accordance with an embodiment.

A user such as a driver of the vehicle 101 may send a registration request for services for the vehicle 101 via a portable electronic device that can connect to the IoT cloud 104 including a vehicle, a smartphone or tablet computer (202). The registration request may include identification information of the vehicle such as vehicle identification number (VIN) and vehicle registration number. The communication between the vehicle 101 and the IoT cloud 104 may be accomplished using various application communication protocols including, for example, Dedicated Short Range Communication (DSRC)/IEEE802.11p, Long Term Evolution-Vehicle to X (LTE-V2X), and fifth generation (5G) wireless communication protocol.

The data feeding module 1051 on the cloud 104 may receive the registration request (204). The data feeding module 1051 may serve as the communication interface between the vehicle 101 and the cloud server 105 on the end of IoT cloud 101. The data feeding module 1051 may be implemented as a distributed event streaming platform for data pipeline which provides a unified, high-throughput, low-latency platform for handling real-time data feeds. In an example, the data feeding module 1051 is implemented with Apache Kafka.

Then, the data feeding module 1051 may feed the registration request to SIS module 1052. In response to receiving the registration request, the SIS module 1052 may determine a geographical location (206) of the vehicle 101 based on the registration request. In an implementation, the registration request may include the geographical location information of the vehicle 101, and the SIS module 1052 may extract the geographical location of the vehicle 101 from the registration request. In another implementation, the SIS module 1052 may infer the geographical location of the vehicle 101 based on network address, such as Internet Protocol address, of a message carrying the registration request.

Figure 3:
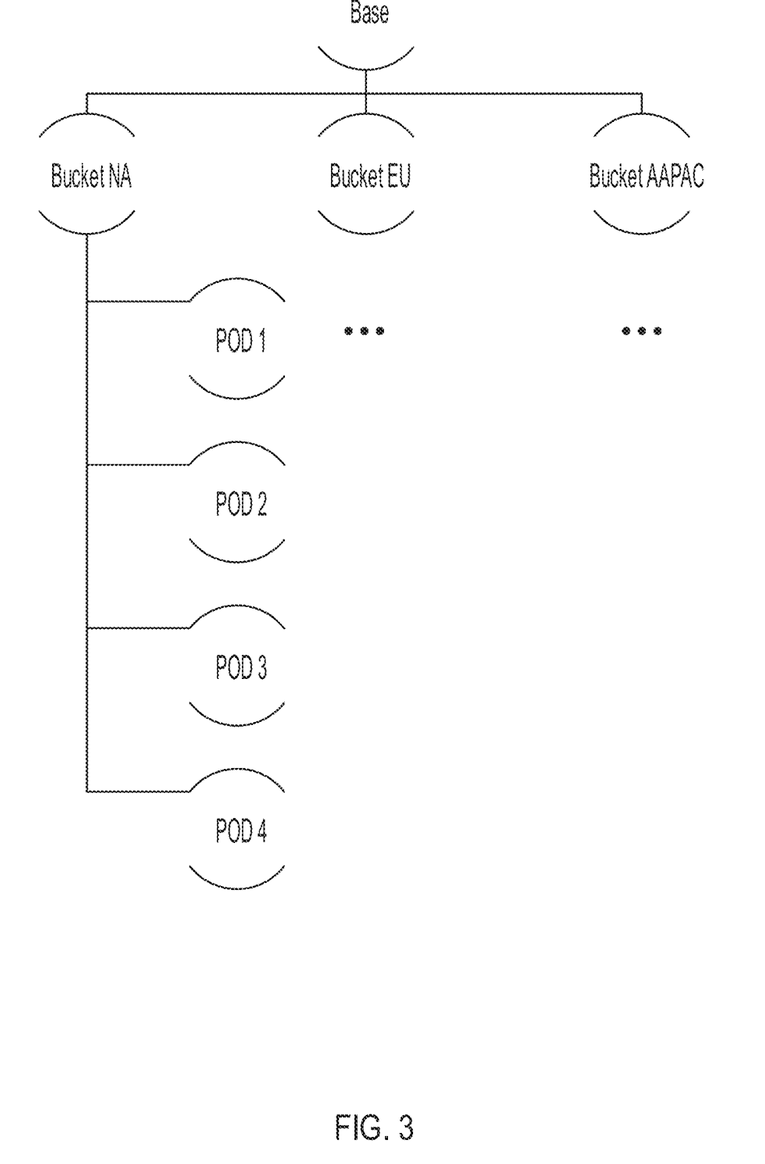
FIG. 3 illustrates a decision tree for cloud services available to a geographical region in accordance with an embodiment.

The SIS module 1052 may identify cloud services available to the geographical location (208). In an implementation, the SIS module 1052 may make use of a decision tree as shown in FIG. 3 to determine identify the cloud services available to the geographical location. For example, the SIS module 1052 may determine the geographical region to which the geographical location belongs. Where the geographical location is California of the United States, the geographical region is determined to be North America. The SIS module 1052 may index the cloud services in the bucket North America in FIG. 3, which are represented as POD 1, POD 2, POD 3, and POD 4. The cloud services may include, for example, a geographical tracking service, a health monitoring service, a vehicle monitoring service, and a teleoperation service.

The IoT system 100 may further include an IoT edge component 103. To facilitate the interaction between the vehicle 101 and the IoT cloud server 105, the SIS module 1052 may deploy an IoT edge component 103 on the vehicle 101 (210). The IoT edge component 104 may represent a software stack extending the artificial intelligence cloud services provided on the IoT cloud 104 and serve as a real time data communication interface between the vehicle 101 and the IoT cloud server 105 on the end of the vehicle 101. In an implementation, the IoT edge component 103 may be integrated with the ECU 102 and fetch the real time series data of the vehicle 101 from the ECU 102. The real time series data may include data generated by various functional units of the vehicle 101 in operation. For example, the function units may include location sensing units, health parameter sensing units, driving control units, and autonomous driving control units.

The vehicle 101 may maintain transmitting the real time series data to the cloud server 105 (211). The SIS module 1052 may extract capability information of the vehicle 101 from the real time series data of the vehicle 101, for example, transmitted via the IoT edge component 103 (212). The capability information of the vehicle 101 may include, for example, global positioning system (GPS) sensing, 360-degree viewing, vehicle automatic transmission, and autopilot features.

Then, the SIS module 1052 may determine cloud services applicable to the vehicle 101 from the cloud services available to the geographical location based on the extracted capability information of the vehicle 101 (214). For example, to determine if the geographical tracking service is applicable, the SIS module 1052 may need to check if the vehicle 101 has the GPS sensing capability. To determine if the vehicle monitoring service is applicable, the SIS module 1052 may need to check if the vehicle has the 360-degree viewing capability. To determine if the teleoperation service is applicable, the SIS module 1052 may need to check if the automatic transmission capability, 360-degree viewing capability, and auto-piloting capability are available to the vehicle 101.

The vehicle 101 may send a cloud service subscription request to the IoT cloud 104 for example via the IoT edge component 103 (216). Where the cloud service specified in the service subscription request is applicable to the vehicle, the SIS module 1052 may provision the requested cloud service on the vehicle based on the real time series data received from the vehicle 101 (218). Otherwise, the SIS module 1052 may decline to provision the requested cloud service on the vehicle 101.

In provisioning services, the SIS module 1052 may make use of machine learning regression algorithms for various cloud services to extract the insight data from the incoming real time series data. Regression analysis is a form of predictive machine learning modelling technique which investigates the relationship between a dependent (target) and independent variable (s) (predictor). It can be used for time series modelling, forecasting, and finding the causal effect relationship between the variables. For example, the regression analysis may help find the relationship between hasty driving and the number of road accidents by a driver.

Figure 4:
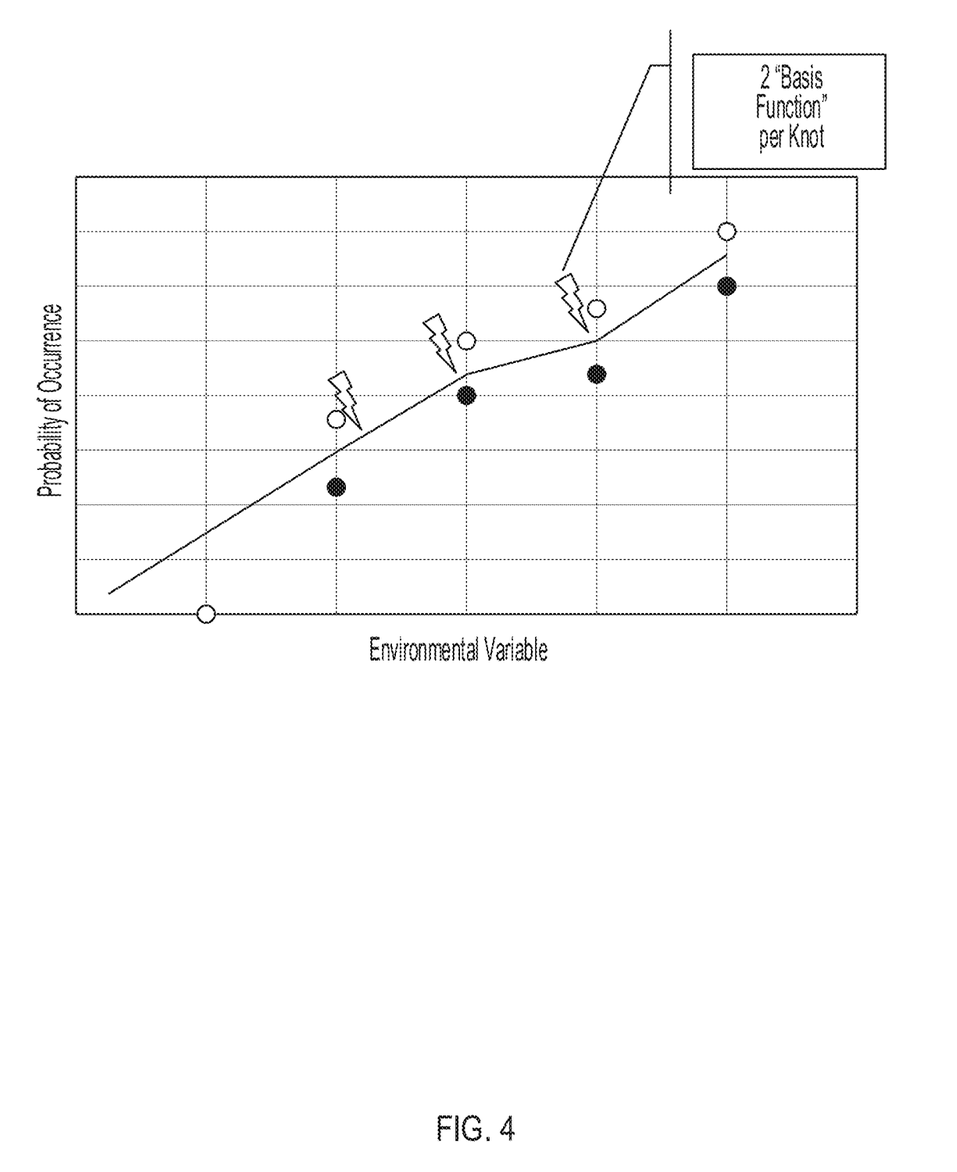
FIG. 4 illustrates the relation between the environmental variables and the predictors in nonlinear regression analysis.

Nonlinear regression does not need to adapt the machine learning model to nonlinear patterns in the data by manually adding model terms, squared terms, or interaction effects. For example, multivariate adaptive regression splines (MARS) is a nonparametric regression which does not make any assumption as to how the dependent variables are related to the predictors. Instead, it may allow the regression function to be "driven" directly from data. As illustrated in FIG. 4, MARS may construct the relation between the dependent and independent variables from a set of coefficients and the basis functions (predictors) such as BF1 and BF2 that are entirely determined from the regression data.

$$BF1=\max(0,\text{Env Var}-\text{Knot})$$

$$BF2=\max(0,\text{Knot}-\text{Env Var})$$

Linear Regression may be used by multiple cloud services where a dependent variable needs to be identified based on independent parameters. For example, to determine the physical state of the driver of the vehicle, a cloud service may need to obtain his body information such as EAR (Eye Aspect Ratio), heart beats, and head position. The time series data would be plotted and if the variance from the mean exceeds the threshold value, the cloud service may infer the occurrence of anomaly in driving behavior.

The SIS module 1052 may store the insight data of the vehicle 101 with respect to the vehicle 101 to the storage module 1053. The storage module 1053 may provide the SIS module 1052 with storage resources to store the insight data of the vehicle 101 within a database or other data structure. In some implementations, the storage module 1053 may be deployed as a cloud-based database platform with the capability to process mass data. Alternatively, or additionally, the storage module 1053 may include data search and analytic tools such as Apache Solr to provide for example real-time indexing and database integration.

In some implementations, the storage module 1053 may also store the real time series data from the vehicle 101. As such, data from the vehicle 101 would be stored locally on the IoT cloud 104. In the absence of a stable network connection between the vehicle 101 and the IoT cloud 104, the SIS module 1052 may switch to provision the cloud service based on the locally stored data, which may ensure availability of seamless vehicle services.

The requested cloud service may include, for example, a geographical tracking service, a health monitoring service, a vehicle monitoring service, and a teleoperation service. In an example, the requested cloud service is a geographical tracking service. The real time series data may include data generated by a location sensing unit of the vehicle 101. The location sensing unit may include, for example, a GPS sensor. The vehicle 101 may maintain transmitting its real time series data to the IoT cloud 104. As a result, the SIS module 1052 may extract real time geographical location information of the vehicle 101 from the real time series data. For example, the real time series data may be organized in an extensible markup language (XML) format with a pre-defined XML metadata. The geographical location data generated by the location sensing unit may be assigned one or more specific XML tags. In this way, the SIS module 1052 may parse the XML data and extract the real time geographical location information based on the specific XML tags.

Subsequently, the SIS module 1052 may identify a traffic condition on the route of the vehicle 101 based on the extracted real time geographical location information. If the identified traffic condition indicates a traffic jam or a natural calamity, the SIS module 1052 may generate an alternate route for the vehicle 101. In an example, where the vehicle 101 is heading towards a traffic jam on a highway, the SIS module 1052 may identify the traffic jam by heavy density of vehicles on the real time geographical location, for example, using the cluster K-means algorithm. The cluster K-means algorithm is an iterative algorithm that partitions the dataset into K pre-defined distinct non-overlapping subgroups (clusters) where each data point belongs to only one group. As the geographical tracking service is enabled on the vehicle 101, the SIS module 1052 may provide to the vehicle 101 an alert of the upcoming traffic jam and suggest an alternative path via the IoT edge component 103, as shown in the example routine in Table 1.

TABLE 1

| Example Routine for Geographical Tracking Service |
| --- |
| RealTimeAdversary(VehicleLocation)<br>{<br>  RouteCluster = FetchRouteConditionAhead(p_VehicleLocation);<br>  If(RouteCluster = jamSituation)<br>  {<br>    SuggestAlternateRoute( );<br>  }<br>  Else If (Routeauster = naturalCalamity)<br>  {<br>    SuggestAlternateRoute( );<br>  }<br>  Else<br>    //ContinueOnRoute;<br>} |

In another example, the requested cloud service is a health monitoring service. The real time series data may include data generated by health parameter sensing units of the vehicle 101. The health parameter sensing units may sense the health data of the driver including, for example, EAR (Eye Aspect Ratio), heart beats, body temperature, and head position. The health parameter sensing units may include, for example, an in-vehicle camera, infrared thermometer, and various biometric sensors. The vehicle 101 may timely collect the health data from the health parameter sensing units and maintain transmitting the real time series data to the IoT cloud 104. As a result, the SIS module 1052 may extract health information of the driver of the vehicle 101 from the real time series data. Then, the SIS module 1052 may determine a health status of the driver based on the extracted health information. In response to an abnormal health status, the SIS module 1052 may trigger an alert on the health status of the driver.

Figure 5:
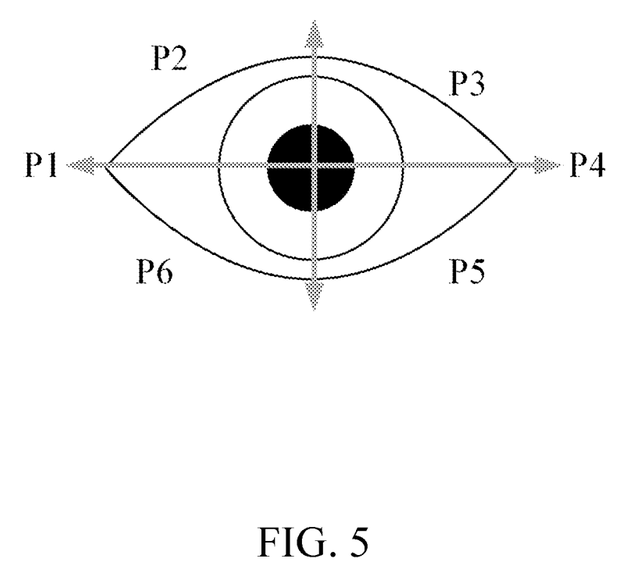
FIG. 5 illustrates the six coordinates for a human eye for calculating eye aspect ratio.

The abnormal health status may include eye closure of the driver. The SIS module 1052 may determine the abnormal health status by measuring the EAR of the driver based on the health information extracted from the real time series data. In one example, each eye is represented by six two-dimension (2D) coordinates P1, P2, P3, P4, P5, and P6, as shown in FIG. 5, starting at the left corner of the eye and then working clockwise around the remainder of the region. EAR may be calculated by the Equation 1 below.

$$EAR = \frac{(P2 - P6) + (P3 - P5)}{2(P1 - P4)} \quad \text{Equation 1}$$

Where, P1, . . . , P6 are 2D facial landmark locations.

The numerator of the Equation 1 computes the distance between the vertical eye landmarks while the denominator computes the distance between horizontal eye landmarks. The denominator is weighted appropriately because there is only one set of horizontal points but two sets of vertical points. As indicated, the EAR may rapidly fall to zero when the eye is closed. In this case, the SIS module 1052 may trigger an alarm event to the vehicle 101 via the IoT edge component 103 and then the vehicle 101 may generate an alarm to the driver.

The abnormal health status may include injury of the driver. The injury of the driver may be indicated by, for example, the abnormal heartbeat rate and the low blood glucose level. The SIS module 1052 may determine the abnormal health status by comparing the readings of the heartbeat and blood glucose level of the driver or the passenger with the normal biometric benchmark values. As a response, the SIS module 1052 may identify a health care institution closest to the vehicle 101 based on the real time geographical location of the vehicle 101 and enable the vehicle 101 to transmit the health information of the driver or passenger to the health care institution.

Figure 6:
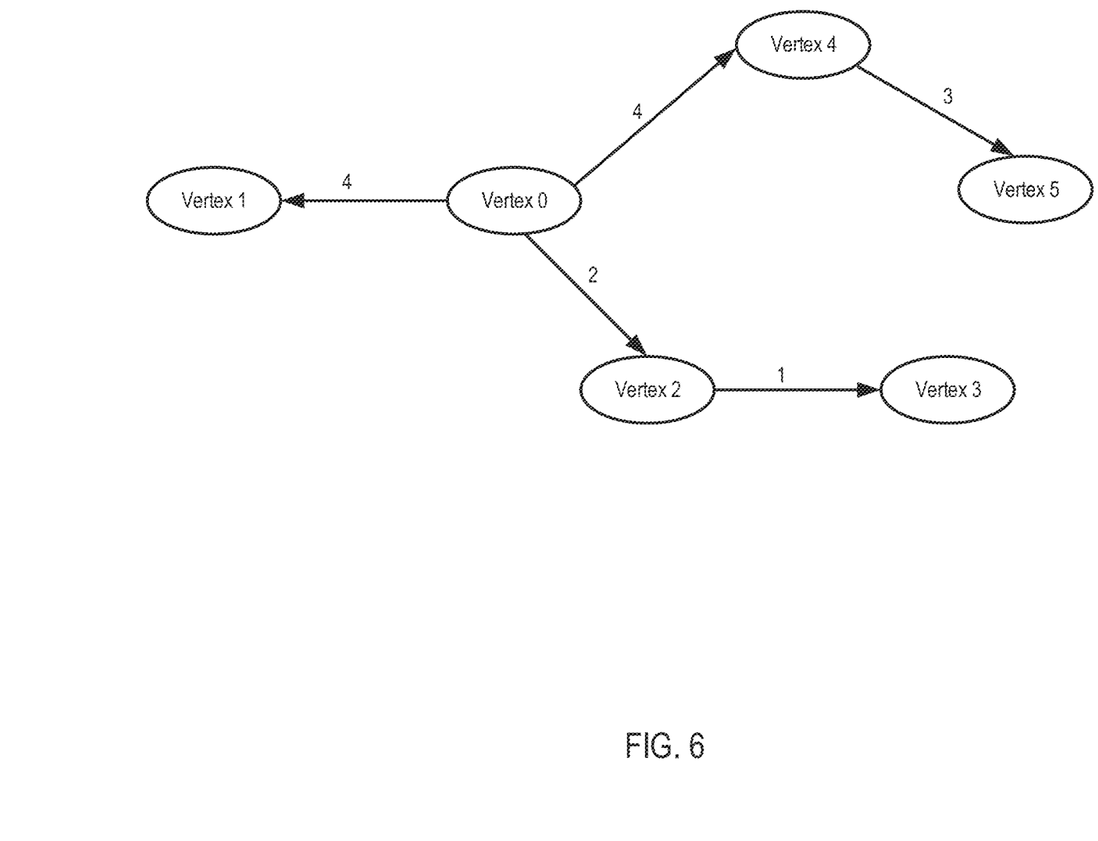
FIG. 6 illustrates an exemplary graph for searching for the shortest path.

The SIS module 1052 may make use of, for example, the Dijkstra's shortest path algorithm to identify the closest health care institution to the vehicle 101. With reference to FIG. 6, the spatial set sptSet is initially empty and distances assigned to the connections between vertices 0 through 6 are {0, INF, INF, INF, INF, INF, INF, INF}, where INF indicates infinite. Now the SIS module 1052 may pick the vertex with minimum distance value as starting point. The vertex 0 is picked, which may for example represent the geographical location of the vehicle 101. The vertices 1, 3, and 5 may represent the neighboring health care institutions. The SIS module 1052 may include vertex 0 into sptSet, which becomes {0}.

After including 0 into the sptSet, the SIS module 1052 may update distance to its adjacent vertices, e.g., vertex 1 and vertex 2. The distance to vertex 1 is updated as 4 and the distance to vertex 2 is updated as 2. Then, the SIS module 1052 include the vertex 1 and the vertex 2 into the spatial set. Likewise, all the vertex nodes are added to the spatial set. In this way, the SIS module 1052 may calculate the spatial values between two vertices and identify the shortest path, i.e., the path vertex 0-vertex 2-vertex 3. Upon determining the closest heath care institution, the SIS module 1052 may, for example, establish a real time data communication link between the vehicle 101 and the closest health care institution via the IoT cloud 104. In an example, the SIS module 1052 may forward the real time series data received from the vehicle 101 to the closest health care institution.

In another example, the requested cloud service is a vehicle monitoring service. The real time series data may include data generated by driving control units of the vehicle 101. The driving control units may include, for example, engine and emission management unit, vehicle stability unit, traction control unit, lane departure warning unit, and auto distance cruise control unit. The vehicle 101 may collect the real time series data generated from the individual driving control units and transmitting the real time series data to the IoT cloud 104 via the IoT edge component 104. As such, the SIS module 1052 may extract driving diagnostic information from the real time series data. The driving diagnostic information may include, for example, speed, acceleration, tire tread depth, brake frequency, rotations per minute (RPMs), and crash-to-safe ratio through distance calculations.

The SIS module 1052 may enable a cloud service, for example, provided by an insurance company to estimate insurance premium of the vehicle 101 based on the driving diagnostic information. For example, the SIS module 1052 may transmit the extracted driving diagnostic information to the insurance premium estimation cloud service and receiving the information on estimated insurance premium from the cloud service. Then, the SIS module 1052 may provide the insurance premium estimation result to the vehicle 101, for example, by displaying the insurance premium estimation result on a user interface of the ITO edge component 103 on the vehicle 101. The process of extracting driving diagnostic information and estimating insurance premium based on the driving diagnostic information may for example be described in U.S. Patent Application Publication No. US2019/0213684 A1 filed Jan. 10, 2018, entitled "Integrated Vehicular Monitoring And Communication System,", which is incorporated by reference herein in its entirety.

In another example, the requested cloud service is a teleoperation service. The real time series data may include data generated by autonomous driving control units of the vehicle. The autonomous driving control units may include, for example, adaptive cruise control, adaptive front lighting control, automatic braking control, transmission control, engine control, and surround radar control. The SIS module 1052 may enable the teleoperation service to establish a communication connection between the vehicle 101 and the remote control center 106 where a remote operator is located.

When the driver of the vehicle is in a health emergency, teleoperations may allow an operator sitting remotely to take full control of the vehicle. The remote operator may maneuver the vehicle as if sitting inside the vehicle. The operator may, for example, remotely turn steering, press brake and gas pedals, and change gears. To tele-operate a vehicle remotely, a good over the air (OTA) connection needs to be established between the vehicle and the remote center where the operator is located.

In an example, the SIS module 1052 may select the remote control center 106 from a plurality of candidate remote control centers based on for example the physical distance between the vehicle 101 and the candidate remote control centers and the stability of communication connection with the candidate remote control centers. Then, the SIS module 1052 may exchange the identification information and communication connection interfaces of the vehicle 101 and the remote control center 106 there between such that a direct communication connection between the vehicle 101 and the remote control center 106 may be established for the teleoperation. In this way, the real time series data generated by the individual autonomous driving control units of the vehicle 101 may be transmitted to the remote control center 106 via the direct communication connection. Appropriate vehicle controlling instructions may be transmitted from the remote control center 106 to the vehicle 101, which may be executed by the individual autonomous driving control units for autonomous driving.

Figure 7:
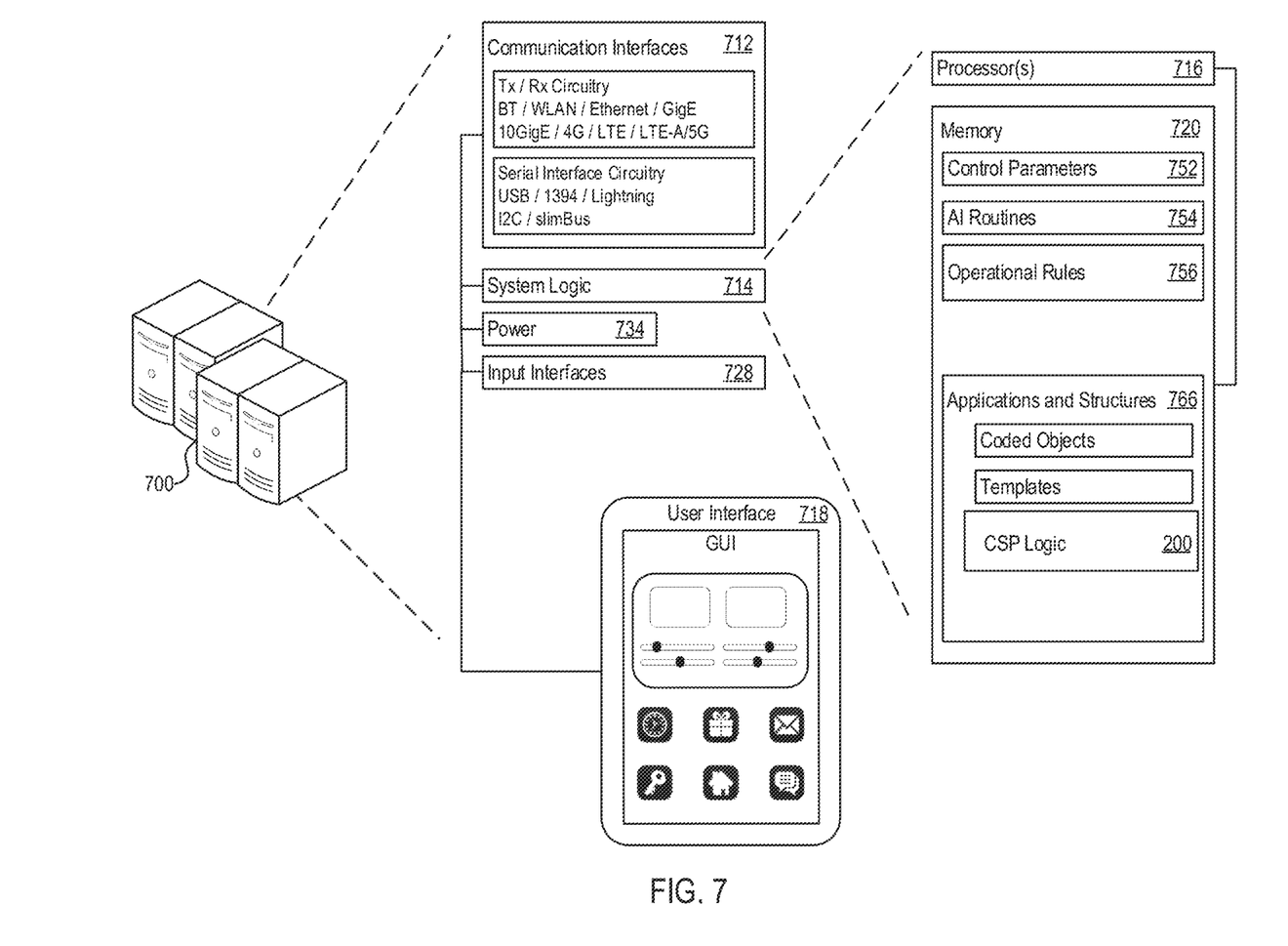
FIG. 7 illustrates an example execution environment for the system provisioning a cloud service on a vehicle.

FIG. 6 shows an example system execution environment 700 for the individual modules in the cloud server 105. The execution environment 700 may include system logic 714 to support execution of the data feeding module 1051, the SIS module 1052, and the storage module 1053 as described above. The system logic 714 may include processors 716, memory 720, and/or other circuitry.

The memory 720 may include control parameters 752, AI routines 754, and operational rules 756. The memory 620 may further include applications and structures 766, for example, coded objects, machine instructions, templates, or other structures to support identifying cloud services available to a geographical region, extracting capability information of the vehicle, determining cloud services applicable to the vehicle, and provisioning applicable cloud services on the vehicle. The applications and structures may implement the CSP logic 200 executed by the cloud server 105.

The execution environment 700 may also include communication interfaces 712, which may support wireless, e.g. Bluetooth, Wi-Fi, WLAN, cellular (4G, LTE/A, 5G), and/or wired, Ethernet, Gigabit Ethernet, optical networking protocols. The communication interfaces 712 may also include serial interfaces, such as universal serial bus (USB), serial ATA, IEEE 1394, lighting port, I$^2$C, slimBus, or other serial interfaces. The communication interfaces 712 may be used to support and/or implement remote operation of user interface. The execution environment 700 may include power functions 734 and various input interfaces 728. The execution environment may also include a user interface 618 that may include human-to-machine interface devices and/or graphical user interfaces (GUI). The user interface 718 may be used to support and/or implement local operation of user interface. In various implementations, the system logic 714 may be distributed over one or more physical servers, be implemented as one or more virtual machines, be implemented in container environments such as Cloud Foundry or Docker, and/or be implemented in Serverless (functions as-a-Service) environments.

The execution environment 700 may be a specially defined computational system deployed in a cloud platform such as the IoT cloud 104. In some cases, the parameters defining the execution environment may be specified in a manifest for cloud deployment. The manifest may be used by an operator to requisition cloud based hardware resources, and then deploy the software components, for example, the SIS module 1052, of the execution environment onto the hardware resources. In some cases, a manifest may be stored as a preference file such as a YAML (yet another mark-up language), JSON, or other preference file type. Additionally or alternatively, the manifest may include custom scripts to implement the JLO stack 200 in a serverless environment.

The methods, devices, processing, circuitry, and logic described above may be implemented in many different ways and in many different combinations of hardware and software. For example, all or parts of the system, including the network interface circuitry and the optimization circuitry, may be circuitry that includes an instruction processor, such as a Central Processing Unit (CPU), microcontroller, or a microprocessor; or as an Application Specific Integrated Circuit (ASIC), Programmable Logic Device (PLD), or Field Programmable Gate Array (FPGA); or as circuitry that includes discrete logic or other circuit components, including analog circuit components, digital circuit components or both; or any combination thereof. The circuitry may include discrete interconnected hardware components or may be combined on a single integrated circuit die, distributed among multiple integrated circuit dies, or implemented in a Multiple Chip Module (MCM) of multiple integrated circuit dies in a common package, as examples.

Accordingly, the circuitry may store or access instructions for execution, or may implement its functionality in hardware alone. The instructions may be stored in a tangible database service medium that is other than a transitory signal, such as a flash memory, a Random Access Memory (RAM), a Read Only Memory (ROM), an Erasable Programmable Read Only Memory (EPROM); or on a magnetic or optical disc, such as a Compact Disc Read Only Memory (CDROM), Hard Disk Drive (HDD), or other magnetic or optical disk; or in or on another machine-readable medium. A product, such as a computer program product, may include a database service medium and instructions stored in or on the medium, and the instructions when executed by the circuitry in a device may cause the device to implement any of the processing described above or illustrated in the drawings.

Implementations of the system may be distributed. For instance, the circuitry may include multiple distinct system components, such as multiple processors and memories, and may span multiple distributed processing systems. Parameters, databases, and other data structures may be separately stored and managed, may be incorporated into a single memory or database, may be logically and physically organized in many different ways, and may be implemented in many different ways. Example implementations include linked lists, program variables, hash tables, arrays, records (e.g., database records), objects, and implicit storage mechanisms. Instructions may form parts (e.g., subroutines or other code sections) of a single program, may form multiple separate programs, may be distributed across multiple memories and processors, and may be implemented in many different ways. Example implementations include standalone programs, and as part of a library, such as a shared library like a Dynamic Link Library (DLL). The library, for example, may contain shared data and one or more shared programs that include instructions that perform any of the processing described above or illustrated in the drawings, when executed by the circuitry.

We claim:

1. A method for provisioning a cloud service on a vehicle, the method comprising:
   in response to receiving a registration request for cloud services for the vehicle, determining, with a processor circuitry of a cloud server communicatively coupled with the vehicle, a current geographical location of the vehicle based on the registration request;
   identifying, with the processor circuitry, cloud services available to the current geographical location;
   extracting, with the processor circuitry, capability information of the vehicle from real time series data of the vehicle, the real time series data including data generated by functional units of the vehicle in operation of the vehicle;
   determining, with the processor circuitry, cloud services applicable to the vehicle from the cloud services available to the current geographical location based on the extracted capability information of the vehicle; and
   in response to receiving a service subscription request from the vehicle, provisioning, with the processor circuitry, on the vehicle a cloud service applicable to the vehicle corresponding to the service subscription request.

2. The method of claim 1, wherein identifying the cloud services available to the current geographical location comprises:
   identifying a geographical region to which the current geographical location belongs; and
   indexing the cloud services available to the current geographical location with the identified geographical region.

3. The method of claim 1, further comprising:
   in response to the registration request, deploying an internet of things (IoT) edge component on the vehicle, the IoT edge component serving as a communication interface between the vehicle and the cloud services applicable to the vehicle.

4. The method of claim 3, further comprising:
   receiving the real time series data of the vehicle via the IoT edge component.

5. The method of claim 1, wherein the registration request comprises identification information of the vehicle, receiving the registration request for the vehicle for cloud services comprises:
   receiving the registration request for the vehicle for cloud services from the vehicle; and
   the method further comprises deriving the current geographical location of the vehicle based on network address of a message carrying the registration request.

6. The method of claim 1, further comprising:
   in response to the cloud service corresponding to the service subscription request being not applicable to the vehicle, declining to provision the cloud service on the vehicle.

7. The method of claim 1, wherein the cloud service is a geographical tracking service, the real time series data comprises data generated by a location sensing unit of the vehicle, and the method further comprises:
   extracting real time geographical location information of the vehicle from the real time series data;
   identifying traffic condition on route of the vehicle based on the extracted real time geographical location information; and
   in response to an identified traffic condition indicating a traffic jam or a natural calamity, generating an alternate route for the vehicle.

8. The method of claim 1, wherein the cloud service is a health monitoring service, the real time series data comprises data generated by health parameter sensing units of the vehicle, and the method further comprises:
   extracting health information of a driver of the vehicle from the real time series data;
   determining a health status of the driver based on the health information; and
   in response to an abnormal health status, triggering an alert on the health status of the driver.

9. The method of claim 8, wherein the abnormal health status is eye closure of the driver, and triggering the alert on the health status of the driver comprises:
   controlling the vehicle to generate an alarm to the driver.

10. The method of claim 8, wherein the abnormal health status is injury of the driver, and triggering the alert on the health of the driver comprises:
    identifying a health care institution closest to the vehicle based on the current geographical location; and
    enabling the vehicle to transmit the health information of the driver to the health care institution.

11. The method of claim 1, wherein the cloud service is a vehicle monitoring service, the real time series data comprises data generated by driving control units of the vehicle, and the method further comprises:
    extracting driving diagnostic information from the real time series data; and
    enabling the cloud service to estimate insurance premium of the vehicle based on the driving diagnostic information.

12. The method of claim 1, wherein the cloud service is a teleoperation service, the real time series data comprises data generated by autonomous driving control units of the vehicle, and the method further comprises:
    enabling the cloud service to establish a communication connection between the vehicle and a remote control center where a remote operator is located.

13. A system for provisioning a cloud service on a vehicle, comprising:
    a memory having stored thereon executable instructions;
    a processor in communication with the memory, the processor when executing the instructions configured to:
    in response to receiving a registration request for cloud services for the vehicle, determine a current geographical location of the vehicle based on the registration request;
    identify cloud services available to the current geographical location;
    extract capability information of the vehicle from real time series data of the vehicle, the real time series data including data generated by functional units of the vehicle in operation of the vehicle;
    determine cloud services applicable to the vehicle from the cloud services available to the current geographical location based on the extracted capability information of the vehicle; and
    in response to receiving a service subscription request from the vehicle, provision on the vehicle a cloud service applicable to the vehicle corresponding to the service subscription request.

14. The system of claim 13, wherein the processor is configured to:
    identify a geographical region to which the current geographical location belongs; and index the cloud services available to the current geographical location with the identified geographical region.

15. The system of claim 13, the processor is further configured to:
in response to the registration request, deploy an internet of things (IoT) edge component on the vehicle, the IoT edge component serving as an communication interface between the vehicle and the cloud services applicable to the vehicle.

16. The system of claim 13, wherein the cloud service is geographical tracking service, the real time series data comprises data generated by a location sensing unit of the vehicle, and the processor is further configured to:
extract real time geographical location information of the vehicle from the real time series data;
identify traffic condition on route of the vehicle based on the extracted real time geographical location information; and
in response to a identified traffic condition indicating a traffic jam or a natural calamity, generate an alternate route for the vehicle.

17. The system of claim 13, wherein the cloud service is a health monitoring service, the real time series data comprises data generated by health parameter sensing units of the vehicle, and the processor is further configured to:
extract health information of a driver of the vehicle from the real time series data;
determine health status of the driver based on the extracted health information; and
in response to an abnormal health status, trigger an alert on the health status of the driver.

18. The system of claim 13, wherein the cloud service is a vehicle monitoring service, the real time series data comprises data generated by driving control units of the vehicle, and the processor is further configured to:
extract driving diagnostic information from the real time series data; and
enable the cloud service to estimate insurance premium of the vehicle based on the driving diagnostic information.

19. The system of claim 13, wherein the cloud service is teleoperation service, the real time series data comprises data generated by autonomous driving control units of the vehicle, and the processor is further configured to:
enable the cloud service to establish a communication connection between the vehicle and a remote control center where a remote operator is located.

20. A product including:
a non-transitory machine-readable media; and
instructions stored on the non-transitory machine-readable media, the instructions configured to, when executed, cause a processor to:
in response to receiving a registration request for cloud services for a vehicle, determine a current geographical location of the vehicle based on the registration request;
identify cloud services available to the current geographical location;
extract capability information of the vehicle from real time series data of the vehicle, the real time series data including data generated by functional units of the vehicle in operation of the vehicle;
determine cloud services applicable to the vehicle from the cloud services available to the current geographical location based on the extracted capability information of the vehicle; and
in response to receiving a service subscription request from the vehicle, provision on the vehicle a cloud service applicable to the vehicle corresponding to the service subscription request.

\* \* \* \* \*